United States Patent
Yamada et al.

(10) Patent No.: US 10,760,904 B2
(45) Date of Patent: Sep. 1, 2020

(54) WEARABLE DEVICE, POSTURE MEASUREMENT METHOD, AND NON-TRANSITORY RECORDING MEDIUM

(71) Applicant: ALPS ALPINE CO., LTD., Tokyo (JP)

(72) Inventors: Yukimitsu Yamada, Miyagi (JP); Daisuke Takai, Miyagi (JP)

(73) Assignee: ALPS ALPINE CO., LTD., Tokyo (JP)

( * ) Notice: Subject to any disclaimer, the term of this patent is extended or adjusted under 35 U.S.C. 154(b) by 324 days.

(21) Appl. No.: 15/945,877

(22) Filed: Apr. 5, 2018

(65) Prior Publication Data

US 2018/0224273 A1 Aug. 9, 2018

Related U.S. Application Data

(63) Continuation of application No. PCT/JP2016/077332, filed on Sep. 15, 2016.

(30) Foreign Application Priority Data

Oct. 14, 2015 (JP) .................. 2015-203215

(51) Int. Cl.
  *G01B 21/22* (2006.01)
  *A61B 5/11* (2006.01)
  (Continued)

(52) U.S. Cl.
  CPC ............ *G01B 21/22* (2013.01); *A61B 5/1116* (2013.01); *A61B 5/1121* (2013.01);
  (Continued)

(58) Field of Classification Search
  CPC .......... A61B 2562/0219; A61B 5/1116; A61B 5/1121; A61B 5/6802; A61B 5/6803; G01B 21/22; G01P 15/0802
  (Continued)

(56) References Cited

U.S. PATENT DOCUMENTS

2002/0095265 A1 7/2002 Satoh et al.
2003/0080976 A1 5/2003 Satoh et al.
(Continued)

FOREIGN PATENT DOCUMENTS

FR 2977353 1/2013
JP 2002-229730 8/2002
(Continued)

OTHER PUBLICATIONS

Extended European Search Report for 16855226.3 dated Aug. 29, 2018.
(Continued)

*Primary Examiner* — John H Le
(74) *Attorney, Agent, or Firm* — IPUSA, PLLC

(57) ABSTRACT

Accelerations (Ax, Ay, Az) in directions along (X', Y', Z') detected by an acceleration sensor 10 are converted, based on a correction angle γ, which is an angle between a first detection axis X' and a first posture axis X, into accelerations (Bx By, Bz) in directions along three posture axes (X, Y, Z). A pitch angle α and a roll angle β, which indicate a posture of a portion to which the wearable device is attached, are calculated based on the accelerations (Bx By, Bz) obtained by the conversion based on the correction angle γ.

7 Claims, 8 Drawing Sheets

(51) Int. Cl.
*A61B 5/00* (2006.01)
*G01P 15/08* (2006.01)

(52) U.S. Cl.
CPC ........ *A61B 5/6802* (2013.01); *G01P 15/0802* (2013.01); *A61B 5/6803* (2013.01); *A61B 2562/0219* (2013.01)

(58) Field of Classification Search
USPC .............. 702/94, 96, 141, 150, 85; 600/301; 33/512; 227/2; 345/629
See application file for complete search history.

(56) References Cited

U.S. PATENT DOCUMENTS

| | | |
|---|---|---|
| 2007/0186429 A1 | 8/2007 | Bonnet et al. |
| 2008/0223895 A1 | 9/2008 | Fujisawa |
| 2008/0288200 A1 | 11/2008 | Noble |
| 2015/0126822 A1 | 5/2015 | Chavan et al. |
| 2015/0282717 A1 | 10/2015 | McCombie et al. |
| 2015/0352437 A1* | 12/2015 | Koseki ................ A63F 13/5255 463/31 |
| 2016/0029943 A1* | 2/2016 | Mizuochi ............. A61B 5/0022 702/141 |

FOREIGN PATENT DOCUMENTS

| | | |
|---|---|---|
| JP | 2003-132374 | 5/2003 |
| JP | 2008-221434 | 9/2008 |

OTHER PUBLICATIONS

International Search Report dated Dec. 13, 2016 in PCT/JP2016/077332 filed on Sep. 15, 2016.

\* cited by examiner

WEARABLE DEVICE, POSTURE MEASUREMENT METHOD, AND NON-TRANSITORY RECORDING MEDIUM

CROSS-REFERENCE TO RELATED APPLICATIONS

The present application is a continuation application of International Application No. PCT/JP2016/077332 filed on Sep. 15, 2016, which claims priority to Japanese Patent Application No. 2015-203215 filed on Oct. 14, 2015. The contents of these applications are incorporated herein by reference in their entirety.

BACKGROUND OF THE INVENTION

1. Field of the Invention

The present invention relates to a wearable device that is wearable on a body, clothing or the like, and particularly relates to a wearable device including an acceleration sensor.

2. Description of the Related Art

As a wearable device, a relatively small electronic device that is wearable on a body, clothing, or the like and that includes a communication function and various sensors (such as an acceleration sensor and an angular velocity sensor) for measuring a state of the body for health management etc. is known, for example (See Patent Document 1 below).

CITATION LIST

Patent Document

[Patent Document 1] Japanese Unexamined Patent Application Publication No. 2008-221434

SUMMARY OF THE INVENTION

Problems to be Solved by the Invention

A wearable device on which an acceleration sensor is mounted can measure, as a posture, a degree of inclination of a portion to which the wearable device is attached (head etc.) with respect to the direction of gravity. The acceleration detected by the acceleration sensor in a state where the portion, to which the wearable device is attached, is stationary indicates a gravitational acceleration. Assuming that the direction of gravity when the portion, to which the wearable device is attached, is in a predetermined reference posture (such as an upright posture) is a "reference direction", the posture of the portion to which the wearable device is attached can be measured, as an inclination degree from the reference posture, by examining a degree by which the direction of gravity indicated by a detection result of the acceleration sensor is inclined with respect to the reference direction as the degree of inclination from the reference posture.

As a method of indicating the posture of an object, a method using a "pitch angle", a "roll angle", a "yaw angle" is known. The "pitch angle" is a rotation angle around a left-right axis that is horizontal to the ground. The "roll angle" is a rotation angle around a front-back axis that is horizontal to the ground. The "yaw angle" is a rotation angle around a vertical axis that is perpendicular to the ground. Three axes serving as references of the "pitch angle", the "roll angle" and the "yaw angle" (which may be referred to as "posture axes" in the following) are orthogonal to each other.

A triaxial acceleration sensor detects respective accelerations in directions along three axes orthogonal to each other (which may be referred to as "detection axes" in the following). If the three detection axes and the three posture axes match with respect to the reference posture, the "pitch angle" and the "roll angle" can be obtained directly from a rotation angle of the gravitational acceleration vector (which may be referred to as the "gravity vector" in the following) around the detection axis.

However, there are various restrictions on a manner of wearing a wearable device on a body and a manner of arranging an acceleration sensor inside the wearable device. Therefore, it may be difficult to match the three detection axes and the three posture axes at the reference posture. In particular, in many cases, two posture axes that are horizontal to the ground are inclined with respect to the left-right direction and the front-back direction. In that case, the "pitch angle" and the "roll angle" around the posture axes horizontal to the ground differ from a rotation angle of the gravity vector around the detection axis. For example, when the posture is changed to change only the "pitch angle" while fixing the "yaw angle" and the "roll angle", the gravity vector does not rotate around the posture axis of the "roll angle", but rotates around the detection axis inclined with respect to this posture axis. Therefore, when obtaining the rotation angle around the detection axis as it is as the "pitch angle" or the "roll angle", there is a disadvantage that the error of a measurement result is large.

The present invention is made in view of the above, and has an object to provide a wearable device, a posture measurement method, and a program that can accurately measure a posture of a portion, to which the wearable device is attached, based on accelerations detected by an acceleration sensor.

Means for Solving the Problems

A wearable device according to a first aspect of the present invention is a wearable device capable of measuring a posture of a portion to which the wearable device is attached including: an acceleration sensor configured to detect respective accelerations in directions along three detection axes that are orthogonal to each other; and a posture angle calculation unit configured to calculate, based on the accelerations detected by the acceleration sensor, a posture angle around at least one posture axis of three posture axes that define a reference of the posture of the portion, to which the wearable device is attached, with respect to a direction of gravity, the three posture axes being orthogonal to each other. A coordinate system obtained by rotating a detection coordinate system, defined by the three detection axes, around one of the detection axes by a correction angle and by moving the detection coordinate system in parallel matches a posture coordinate system defined by the three posture axes. The posture calculation unit converts, based on the correction angle, the accelerations in the directions along the three detection axes detected by the acceleration sensor into accelerations in directions along the three posture axes, and calculates, based on the accelerations at the three posture axes obtained by the conversion, the posture angle around the at least one posture axis.

According to the above-described configuration, the accelerations in the directions along the three detection axes detected by the acceleration sensor are converted, based on the correction angle, into the accelerations in the directions along the three posture axes. The posture angle around the at least one posture axis is calculated based on the accelerations at the three posture axes obtained by the conversion. Therefore, even when the posture axes and the three detection axes do not match, an accurate posture angle is calculated based on the accelerations in the directions along the three detection axes.

Preferably, the above-described wearable device includes an acceleration obtaining unit configured to obtain, upon a signal being input, the accelerations detected by the acceleration sensor, the signal indicating that a predetermined motion of, while maintaining the posture angle at two of the posture axes, changing the posture angle at one of the posture axes that forms the correction angle with one of the detection axes is being performed; and a correction angle calculation unit configured to calculate, based on the accelerations obtained by the acceleration obtaining unit when the predetermined motion is being performed, the correction angle.

According to the above-described configuration, because the correction angle is calculated based on the accelerations detected by the acceleration sensor when the predetermined motion is being performed, even when the correction angle varies depending on a manner of wearing the above-described wearable device and the like, the correction angle is accurately calculated in which the variation is reflected.

Preferably, the three posture axes may be composed of a first posture axis, a second posture axis, and a third posture axis, and the three detection axes may be composed of a first detection axis that forms the correction angle with the first posture axis, a second detection axis that forms the correction angle with the second posture axis, and a third detection axis that forms the correction angle with the third posture axis. The acceleration sensor may detect a first acceleration in a direction along the first detection axis, a second acceleration in a direction along the second detection axis, and a third acceleration in a direction along the third detection axis, respectively. The predetermined motion may be a motion of changing the posture angle at the first posture axis while maintaining the posture angle at the second posture axis and the third posture axis. The correction angle calculation unit may calculate, based on the first acceleration, the second acceleration, and the third acceleration obtained by the acceleration obtaining unit when the predetermined motion is being performed, the correction angle.

Preferably, the correction angle calculation unit may calculate, based on the first acceleration, the second acceleration, and the third acceleration obtained by the acceleration obtaining unit when the predetermined motion is being performed, a first rotation angle around the first detection axis and a second rotation angle around the second detection axis, may calculate a ratio between the first rotation angle and the second rotation angle, and may obtain the correction angle based on the ratio.

Preferably, the correction angle calculation unit may calculate, based on first accelerations, second accelerations, and third accelerations obtained at a plurality of timings when the predetermined motion is being performed, first rotation angles and second rotation angles at the respective timings, may calculate respective ratios between the first rotation angles and the second rotation angles at the plurality of timings, may calculate an average value and a variance of the ratios calculated for the plurality of timings, may set, based on the average value and the variance, an average value range of the ratios, may specify ratios included in the average value range, may calculate an adjusted average value that is an average value of the specified ratios, and may obtain the correction angle based on the adjusted average value.

Preferably, the above-described wearable device may include a storage unit configured to store information for the correction angle used to convert the accelerations in the posture angle calculation unit. Alternatively, the above-described wearable device may include a communication unit configured to process a communication signal including information for the correction angle used to convert the accelerations in the posture angle calculation unit.

A second aspect of the present invention relates to a posture measurement method, by an attached wearable device, for calculating a posture angle around at least one posture axis of three posture axes that define a reference of a posture of a portion, to which the wearable device is attached, with respect to a direction of gravity, the three posture axes being orthogonal to each other. In the posture measurement method, the wearable device includes an acceleration sensor configured to detect respective accelerations in directions along three detection axes that are orthogonal to each other, and a coordinate system obtained by rotating a detection coordinate system, defined by the three detection axes, around one of the detection axes by a correction angle and by moving the detection coordinate system in parallel matches a posture coordinate system defined by the three posture axes. The posture measurement method includes: a step of converting, based on the correction angle, the accelerations in the directions along the three detection axes detected by the acceleration sensor into accelerations in directions along the three posture axes; and a step of calculating, based on the accelerations at the three posture axes obtained by the conversion, the posture angle around the at least one posture axis.

According to the above-described posture measurement method, even when the posture axes and the three detection axes do not match, an accurate posture angle is calculated based on the accelerations in the directions along the three detection axes.

Preferably, the above-described posture measurement method may include a step of obtaining, upon a signal being input, the accelerations detected by the acceleration sensor, the signal indicating that a predetermined motion of, while maintaining the posture angle at two of the posture axes, changing the posture angle at one of the posture axes that forms the correction angle with one of the detection axes is being performed; and a step of calculating the correction angle based on the accelerations obtained in the step of obtaining the accelerations when the predetermined motion is being performed. Thereby, even when the correction angle varies depending on a manner of wearing the above-described wearable device and the like, the correction angle is accurately calculated in which the variation is reflected.

Preferably, the three posture axes may be composed of a first posture axis, a second posture axis, and a third posture axis, and the three detection axes may be composed of a first detection axis that forms the correction angle with the first posture axis, a second detection axis that forms the correction angle with the second posture axis, and a third detection axis that forms the correction angle with the third posture axis. The acceleration sensor may detect a first acceleration in a direction along the first detection axis, a second acceleration in a direction along the second detection axis, and a third acceleration in a direction along the third detection axis, respectively. The predetermined motion may be a motion of changing the posture angle at the first posture axis while maintaining the posture angle at the second posture axis and the third posture axis. In the step of calculating the correction angle, the correction angle may be calculated based on the first acceleration, the second acceleration, and the third acceleration obtained in the step of obtaining the accelerations when the predetermined motion is being performed.

Preferably, in the step of calculating the correction angle, a first rotation angle around the first detection axis and a second rotation angle around the second detection axis may be calculated based on the first acceleration, the second acceleration, and the third acceleration obtained in the step of obtaining the accelerations when the predetermined motion is being performed; a ratio between the first rotation angle and the second rotation angle may be calculated; and the correction angle may be obtained based on the ratio.

Preferably, in the step of calculating the correction angle, based on first accelerations, second accelerations, and third accelerations obtained at a plurality of timings in the step of obtaining the accelerations when the predetermined motion is being performed, first rotation angles and second rotation angles at the respective timings may be calculated; respective ratios between the first rotation angles and the second rotation angles at the plurality of timings may be calculated; an average value and a variance of the ratios calculated for the plurality of timings may be calculated; an average value range of the ratios may be set based on the average value and the variance; ratios included in the average value range may be specified; an adjusted average value that is an average value of the specified ratios may be calculated; and the correction angle may be calculated based on the adjusted average value.

A third aspect of the present invention is a program for causing a computer to execute the posture measurement method according to the above-described second aspect.

Effect of the Invention

According to the present invention, it is possible to accurately measure a posture of a portion, to which a wearable device is attached, based on accelerations detected by an acceleration sensor.

BRIEF DESCRIPTION OF THE DRAWINGS

FIGS. 2A and 2B are diagrams illustrating an example of the wearable device that a user wears, in which FIG. 2A is a view as seen from the right side of the user and FIG. 2B is a view as seen from above the user;

DESCRIPTION OF THE EMBODIMENTS

First Embodiment

Figure 1:
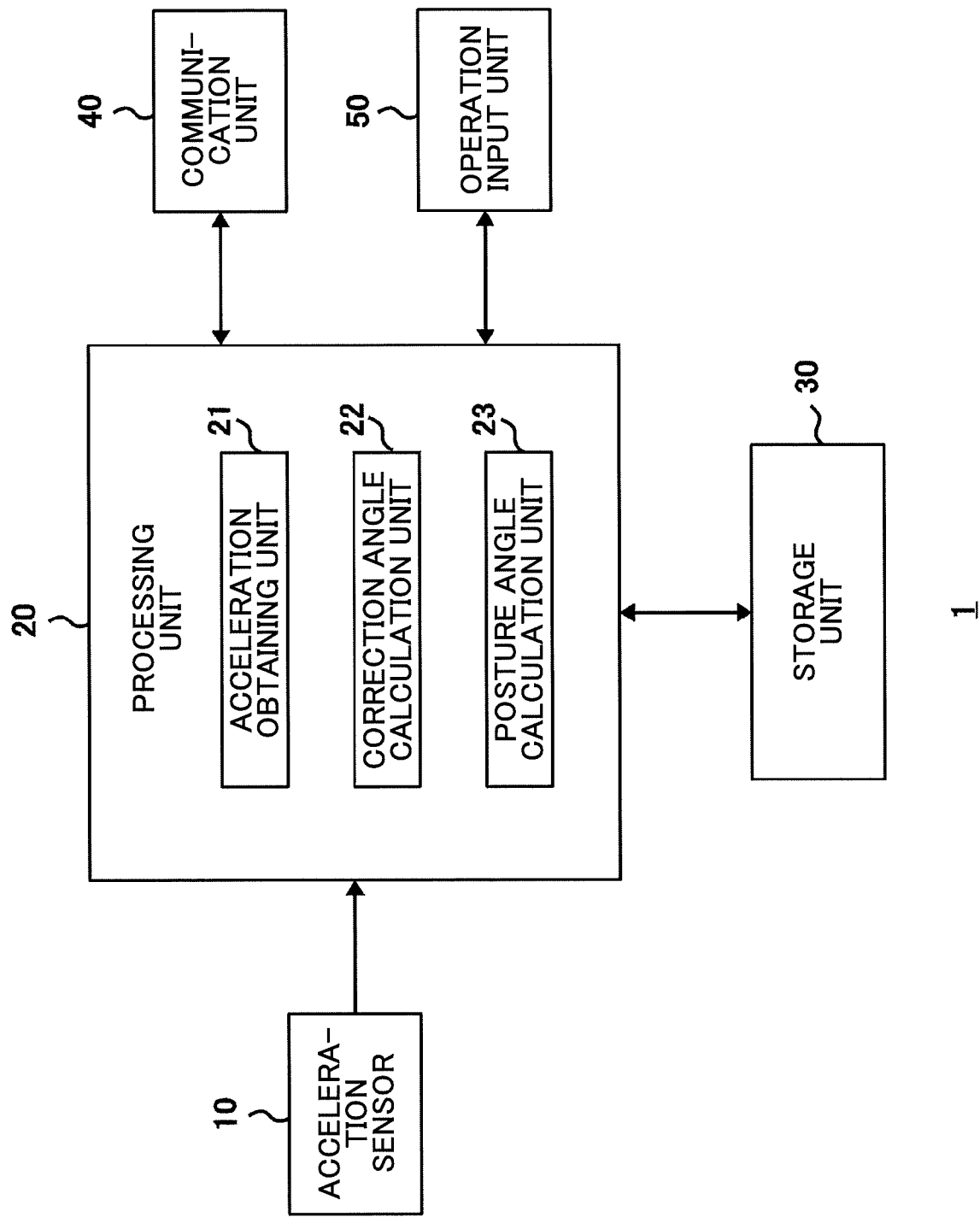
FIG. 1 is a diagram illustrating an example of a configuration of a wearable device according to an embodiment of the present invention.
Figure 2A:
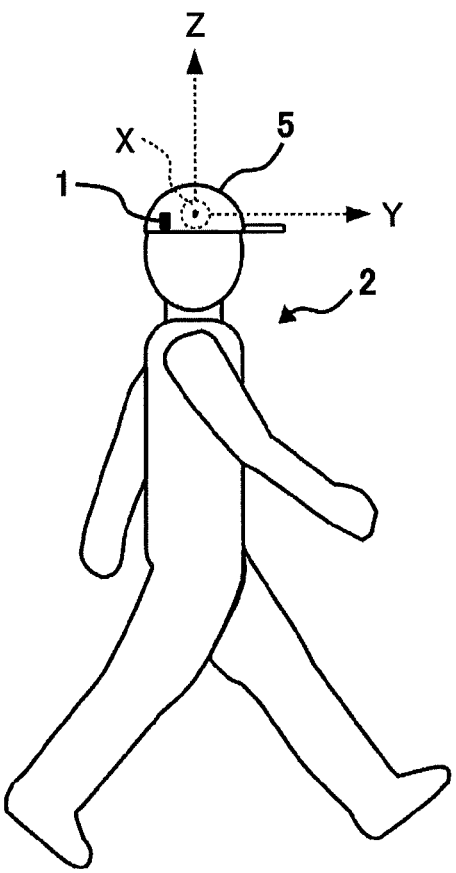
Figure 2B:
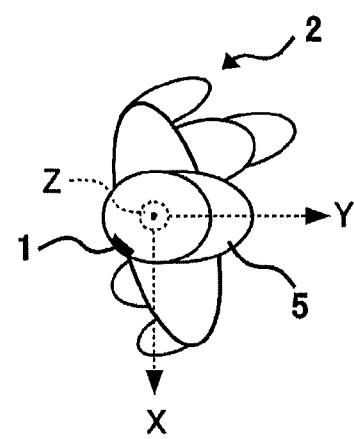

In the following, a wearable device 1 according to a first embodiment of the present invention will be described with reference to the diagrams. FIG. 1 is a diagram illustrating an example of a configuration of the wearable device 1 according to the present embodiment. FIGS. 2A and 2B are diagrams illustrating an example of a method of attaching the wearable device 1.

The wearable device 1 according to the present embodiment measures a posture of a portion, to which the wearable device is attached, based on a detection result of an acceleration sensor. That is, the wearable device 1 obtains, based on a gravity vector detected by the acceleration sensor, posture angles around three posture axes that define a reference of the posture of the portion, to which the wearable device is attached, with respect to a direction of gravity and that are orthogonal to each other (a first posture axis X, a second posture axis Y and a third posture axis Z). In the example of FIGS. 2A and 2B, the wearable device 1 is attached to the right rear side face of a cap 5 that a user 2 wears. Note that the position to which the wearable device 1 is attached is not limited to the example of FIGS. 2A and 2B, and may be a left side face, a top portion, a back face portion, or a brim portion of the cap 5. Also, the wearable device 1 is not limited to being attached to a cap but may also be mounted to a hands-free device, a headset, a hearing aid, or glasses, for example.

The wearable device 1 illustrated in FIG. 1 includes an acceleration sensor 10, a processing unit 20, a storage unit 30, a communication unit 40, and an operation input unit 50.

The acceleration sensor 10 detects respective accelerations (which are a first acceleration Ax, a second acceleration Ay, and a third acceleration Az) in directions along three detection axes (which are a first detection axis X', a second detection axis Y', and a third detection axis Z') that are orthogonal to each other. For example, the acceleration sensor 10 may be configured to include a MEMS (micro electro mechanical systems) based triaxial acceleration sensor. The acceleration sensor 10 repeatedly detects the accelerations in the respective directions under the control of the processing unit 20.

Figure 3:
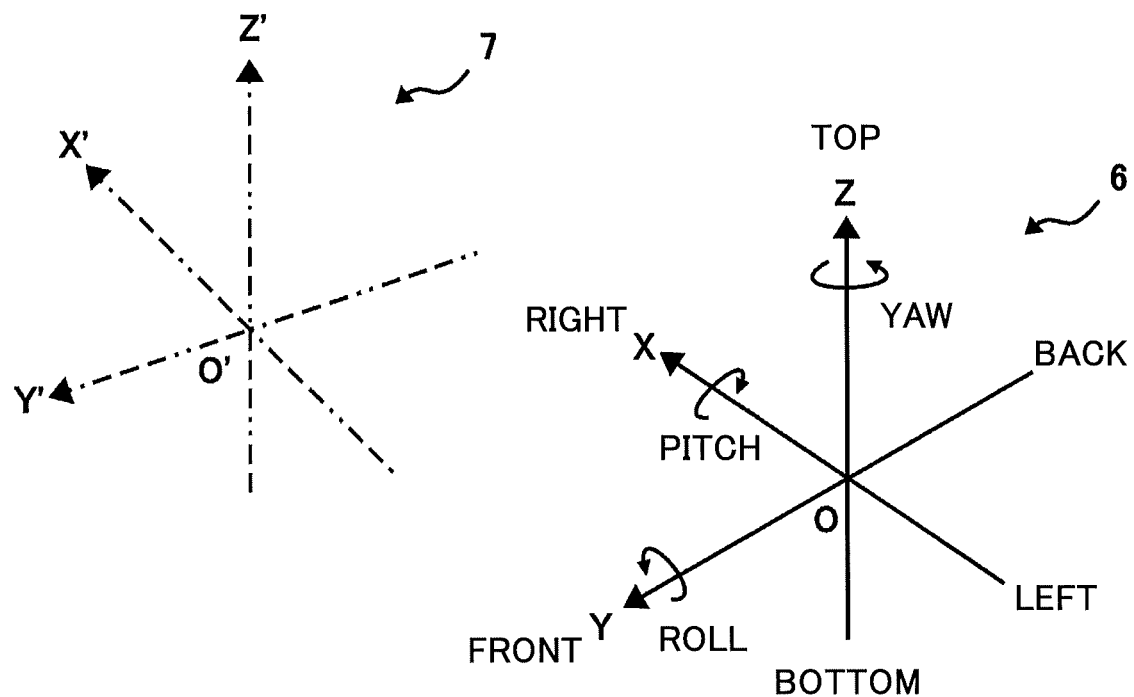
FIG. 3 is a diagram illustrating a relationship between a posture coordinate system and a detection coordinate system.

FIG. 3 is a diagram illustrating a relationship between a posture coordinate system 6 and a detection coordinate system 7. The posture coordinate system 6 is a coordinate system defined by three posture axes (which are a first posture axis X, a second posture axis Y, and a third posture axis Z). The detection coordinate system 7 is a coordinate system defined by three detection axes (which are a first detection axis X', a second detection axis Y', and a third detection axis Z'). As illustrated in FIGS. 2A and 2B, for example, the posture coordinate system 6 is set at the center of the head of the user 2. Therefore, the detection coordinate system 7 of the wearable device 1 attached to the side face of the cap 5 does not match the posture coordinate system 6. In the example of FIGS. 2A and 2B, the origin O' of the detection coordinate system 7 is horizontally displaced towards the right with respect to the origin O of the posture coordinate system 6, and the first detection axis X' is inclined with respect to the first posture axis X. The third detection axis Z' is parallel to the third posture axis Z.

Figure 4:
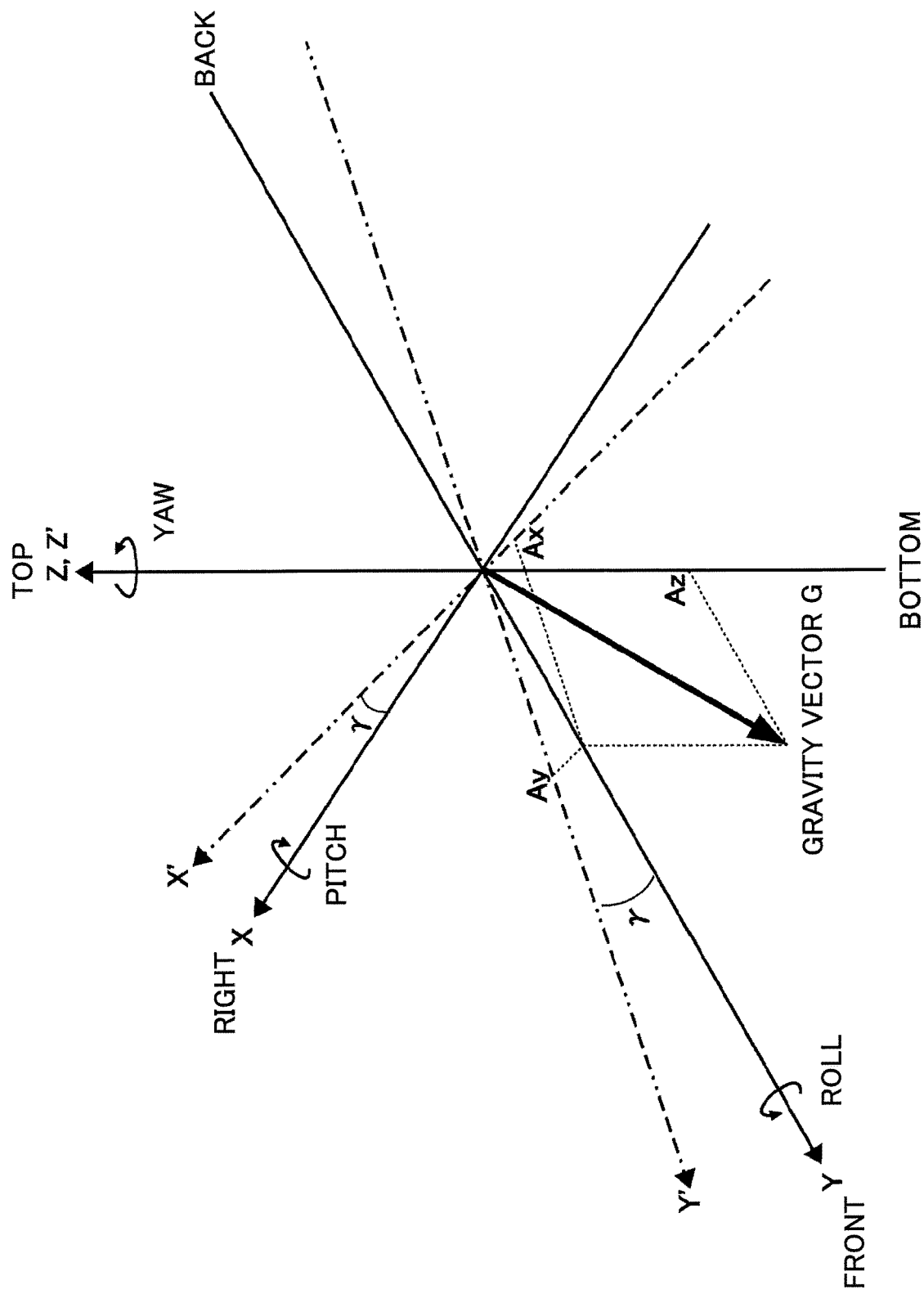
FIG. 4 is a diagram illustrating a state obtained by moving the detection coordinate system in parallel to match an origin of the detection coordinate system and an origin of the posture coordinate system.

FIG. 4 is a diagram illustrating a state obtained by moving the detection coordinate system 7 in parallel to match the origin O' of the detection coordinate system 7 and the origin O of the posture coordinate system 6. As illustrated in FIG. 4, the angle between the first detection axis X' and the first posture axis X is "γ". In the following description, "γ" is referred to as the "correction angle γ".

The communication unit 40 is a device for exchanging data with an external device (not illustrated) using a predetermined communication method. For example, the communication unit 40 may receive, from an external device, a command for causing the processing unit 20 to execute a predetermined process and data to be used for executing the process. Also, the communication unit 40 may transmit to an external device, data representing processing results of the processing unit 20 (e.g., data on the number of steps, data on the period of one step of a walking motion). For example, the communication unit 40 may be configured to include a communication module, such as a Bluetooth (registered trademark) module, that establishes relatively short distance communication with a portable device, such as a smartphone.

The input unit 50 is a device that generates a signal according to an input operation, and includes, for example, buttons, switches, and the like.

The processing unit 20 is a device that controls overall operations of the wearable device 1. The processing unit 20 may be configured to include a computer that executes a process according to a program loaded in the storage unit 30, for example. The program of the storage unit 30 may be stored in advance in a ROM or the like, or may be downloaded from an external device via the communication unit 40. Alternatively, the program may be input from an external source via an interface device, such as a USB, or a recording medium reading device, and written in the storage unit 30. Note that all processes in the processing unit 20 may be executed by a computer, or at least a part of the processes in the processing unit 20 may be executed by a dedicated hardware circuit.

The processing unit 20 includes an acceleration obtaining unit 21, a correction angle calculation unit 22, and a posture angle calculation unit 23 as processing blocks related to measurement of a posture.

When a signal indicating that a predetermined motion is being performed is input in the input unit 50, the acceleration obtaining unit 21 obtains accelerations detected by the acceleration sensor 10. This predetermined motion is a motion of changing a pitch angle, which is a posture angle around the first posture axis X, while maintaining a roll angle, which is a posture angle around the second posture axis Y, and a yaw angle, which is a posture angle around the third posture axis Z. In the example of FIGS. 2A and 2B, this predetermined motion is a motion of raising and lowering one's head. For example, the acceleration obtaining unit 21 obtains accelerations repeatedly detected by the acceleration sensor 10 when a predetermined motion (motion of raising and lowering one's head) is being performed, and stores the obtained accelerations in the storage unit 30.

The correction angle calculation unit 22 calculates a correction angle γ based on the accelerations obtained by the acceleration obtaining unit 21 when the predetermined motion (the motion of raising and lowering one's head) is being performed. For example, the correction angle calculation unit 22 calculates the correction angle γ by the following approximate formula.

$$\gamma = a\sin\{ax/\sqrt{(Ax^2 + Ay^2 + Az^2)}\} \quad (1)$$

In the above formula (1), "Ax" indicates the first acceleration in the direction along the first detection axis X', "Ay" indicates the second acceleration in the direction along the second detection axis Y', and "Az" indicates the third acceleration in the direction along the third detection axis Z'. For example, the correction angle calculation unit 22 calculates, by the formula (1), a plurality of correction angles γ from a plurality of sets of accelerations (Ax, Ay, Az) obtained at a plurality of timings, and outputs an average value of these as a calculation result of the correction angle γ.

Based on the accelerations (Ax', Ay', and Az') detected by the acceleration sensor 10 and the correction angle γ calculated by the correction angle calculation unit 22, the posture angle calculation unit 23 calculates the pitch angle, which is a posture angle around the first posture axis X, and the roll angle, which is a posture angle around the second posture axis Y.

First, the posture angle calculation unit 23 converts the accelerations (Ax, Ay, Az) in the directions along the three detection axes (X', Y', Z') detected by the acceleration sensor 10 into accelerations (Bx, By, Bz) in directions along three posture axes (X, Y, Z). This conversion is expressed by the following formula.

$$\begin{pmatrix} Bx \\ By \\ Bz \\ 1 \end{pmatrix} = \begin{pmatrix} \cos\gamma & -\sin\gamma & 0 & 0 \\ \sin\gamma & \cos\gamma & 0 & 0 \\ 0 & 0 & 1 & 0 \\ 0 & 0 & 0 & 1 \end{pmatrix} \begin{pmatrix} Ax \\ Ay \\ Az \\ 1 \end{pmatrix} \quad (2)$$

In the formula (2), "Bx" indicates the first acceleration in the direction along the first posture axis X, "By" indicates the second acceleration in the direction along the second posture axis Y, and "Bz" indicates the third acceleration in the direction along the third posture axis Z.

Based on the accelerations (Bx, By, Bz) obtained by the conversion by the formula (2), the posture angle calculation unit 23 calculates the pitch angle around the first posture axis X and the roll angle around the second posture axis Y, respectively. The pitch angle "α" the roll angle "β" are respectively expressed by the following formulas.

$$\alpha = a\tan\{By/\sqrt{(Bx^2 + Bz^2)}\} \quad (3)$$

$$\beta = a\tan(Bx/Bz) \quad (4)$$

The storage unit 30 stores computer programs to be executed by the processing unit 20, constant data used by the processing unit 20 in executing a process, variable data temporarily held during execution of a process, and processing result data (e.g., accelerations Ax to Az and correction angles γ), for example. The storage unit 30 may be configured to include a ROM, a RAM, a nonvolatile memory or the like, for example.

Figure 5:
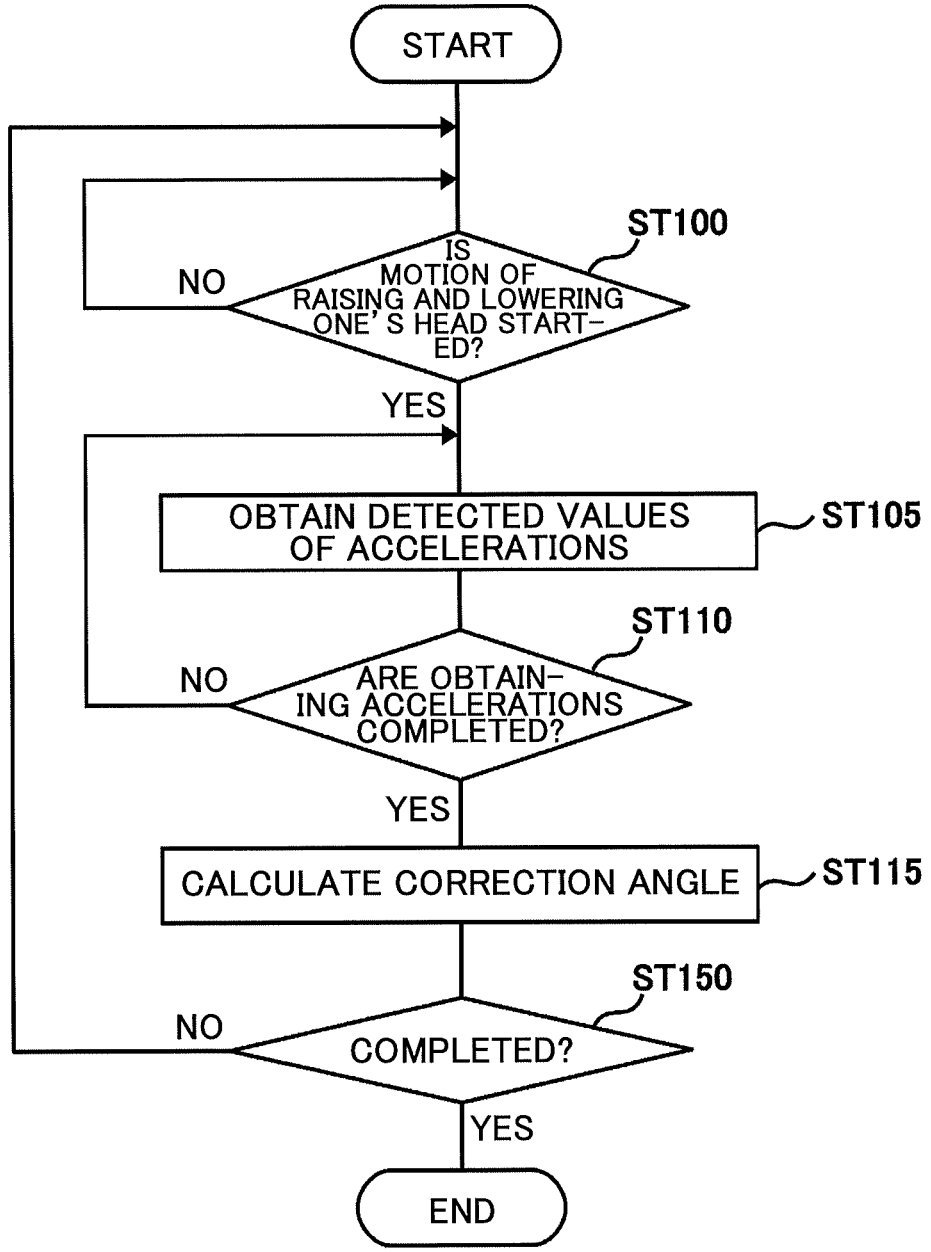
FIG. 5 is a flowchart that describes a calculation process of a correction angle in the wearable device according to a first embodiment.

In the following, operations of the wearable device 1 according to the present embodiment having the above-described configuration will be described. FIG. 5 is a flowchart that describes a calculation process of a correction angle γ in the wearable device 1 according to the first embodiment.

ST100: The acceleration obtaining unit 21 monitors whether a predetermined signal indicating that a predetermined motion (a motion of raising and lowering one's head) is being input has been in the input unit 50. When the signal is input in the input unit 50, the acceleration obtaining unit 21 proceeds to step ST105, otherwise the acceleration obtaining unit 21 remains in step ST100 and continues monitoring.

ST105: The acceleration obtaining unit 21 obtains accelerations (Ax, Ay, Az) detected by the acceleration sensor 10, and proceeds to step ST110.

ST110: The acceleration obtaining unit 21 determines whether obtaining the accelerations (Ax, Ay, Az) have been completed. For example, the acceleration obtaining unit 21 measures an elapsed time after the process shifts to step ST105 from step ST100. When the measured time has exceeded a predetermined time, the acceleration obtaining unit 21 determines that obtaining the accelerations (Ax, Ay, Az) is completed. Alternatively, the acceleration obtaining unit 21 counts the number of times obtaining the accelerations (Ax, Ay, Az) after the process shifts to step ST105 from step ST100. When the measured number of times has exceeded a predetermined number, the acceleration obtaining unit 21 determines that obtaining the accelerations (Ax, Ay, Az) is completed.

ST115: Upon the acceleration obtaining unit 21 completing obtaining the accelerations (Ax, Ay, Az), the correction angle calculation unit 22 calculates a correction angle $\gamma$ based on the obtained accelerations (Ax, Ay, Az). In a case where a plurality of accelerations (Ax, Ay, Az) detected at a plurality of different timings are obtained, the correction angle calculation unit 22 calculates correction angles $\gamma$ for the respective timings by the formula (1). Upon obtaining the plurality of correction angles $\gamma$ calculated for the plurality of timings, the correction angle calculation unit 22 calculates an average value of the plurality of correction angles $\gamma$, and outputs the average value as a calculation result of the correction angle $\gamma$. Note that in this case, the correction angle calculation unit 22 may calculate an average value and a variance of all the correction angles $\gamma$, and may set an average range of the correction angles $\gamma$ based on the calculated average value and the calculated variance. Then, the correction angle calculation unit 22 may further calculate an average value of the correction angles $\gamma$ included in the calculated average range, and may output the average value as the calculation result of the correction angle $\gamma$. Thereby, because correction angles $\gamma$ having large errors that are not included in the average range are excluded, an error of a finally obtained correction angle $\gamma$ is reduced.

Figure 6:
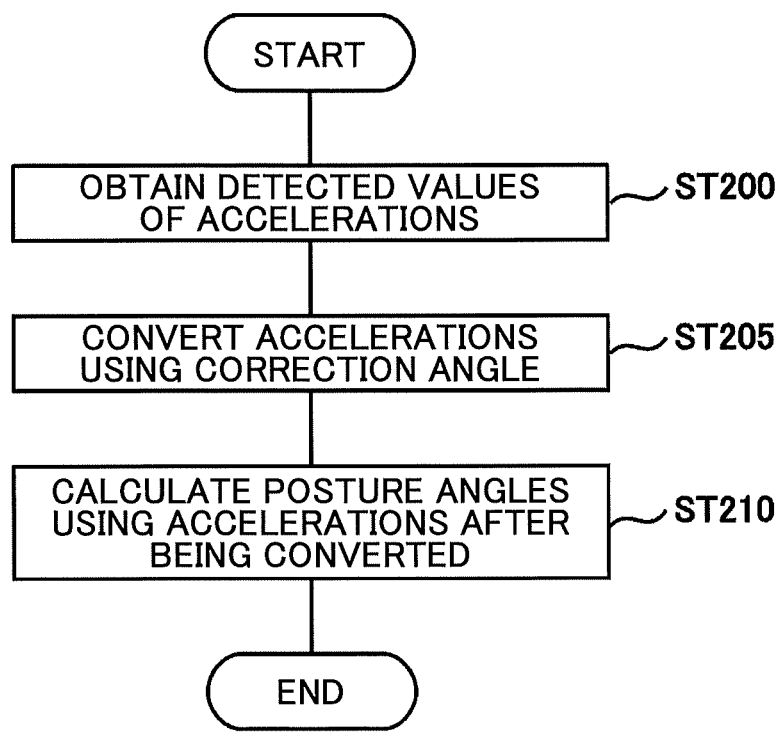
FIG. 6 is a flowchart that describes a calculation process of posture angles in the wearable device according to the embodiment of the present invention.

FIG. 6 is a flowchart that depicts a calculation process of posture angles (a pitch angle and a roll angle) in the wearable device 1 according to the present embodiment.

ST200: The acceleration obtaining unit 21 obtains the accelerations (Ax, Ay, Az) detected by the acceleration sensor 10.

ST205: The posture angle calculation unit 23 performs, for example, matrix calculation of the formula (2) based on the correction angle $\gamma$ calculated by the correction angle calculation unit 22 to convert the accelerations (Ax, Ay, Az) obtained in step ST200 into accelerations (Bx, By, Bz) in the directions along the three posture axes (X, Y, Z).

ST210: Using the accelerations (Bx, By, Bz) obtained in step ST205, the posture angle calculation unit 23 calculates a pitch angle $\alpha$ and a roll angle $\beta$, by the formulas (3) and (4), for example.

As described above, according to the wearable device 1 according to the present embodiment, the accelerations (Ax, Ay, Az) in the directions along (X', Y', Z') detected by the acceleration sensor 10 are converted, based on the correction angle $\gamma$, which is an angle between the first detection axis X' and the first posture axis X, into the accelerations (Bx By, Bz) in the directions along the three posture axes (X, Y, Z). The pitch angle $\alpha$ and the roll angle $\beta$, which indicate a posture of the portion to which the wearable device is attached, are calculated based on the accelerations (Bx By, Bz) obtained by the conversion based on the correction angle $\gamma$. Therefore, even when the posture coordinate system 6 and the detection coordinate system 7 do not match each other, the pitch angle $\alpha$ and the roll angle $\beta$ can be accurately obtained based on the accelerations (Ax, Ay, Az) of the detection coordinate system 7.

Further, according to the wearable device 1 according to the present embodiment, a correction angle $\gamma$ is calculated based on accelerations (Ax, Ay, Az) detected by the acceleration sensor 10 when a predetermined motion (a motion of raising and lowering one's head) is being performed. If a fixed value is used as the correction angle $\gamma$, because a practical correction angle $\gamma$ varies depending on a manner of wearing the wearable device 1 and the like, the fixed value tends to have an error with respect to the practical correction angle $\gamma$, and accuracy of calculating the angles ($\alpha$ and $\beta$) decreases. According to the present embodiment, because it is possible to calculate an accurate correction angle $\gamma$ in which variation is reflected, it is possible to suppress a decrease in the accuracy of calculating the posture angles ($\alpha$ and $\beta$).

Second Embodiment

Next, a second embodiment of the present invention will be described. The wearable device 1 according to the second embodiment is different from the wearable device 1 illustrated in FIG. 1 in the method of calculating a' correction angle in the correction angle calculation unit 22, and other configurations are the same as those of the wearable device 1 illustrated in FIG. 1. In the following, an operation of the correction angle calculation unit 22 differing from that of the wearable device 1 illustrated in FIG. 1 will be described.

Figure 7:
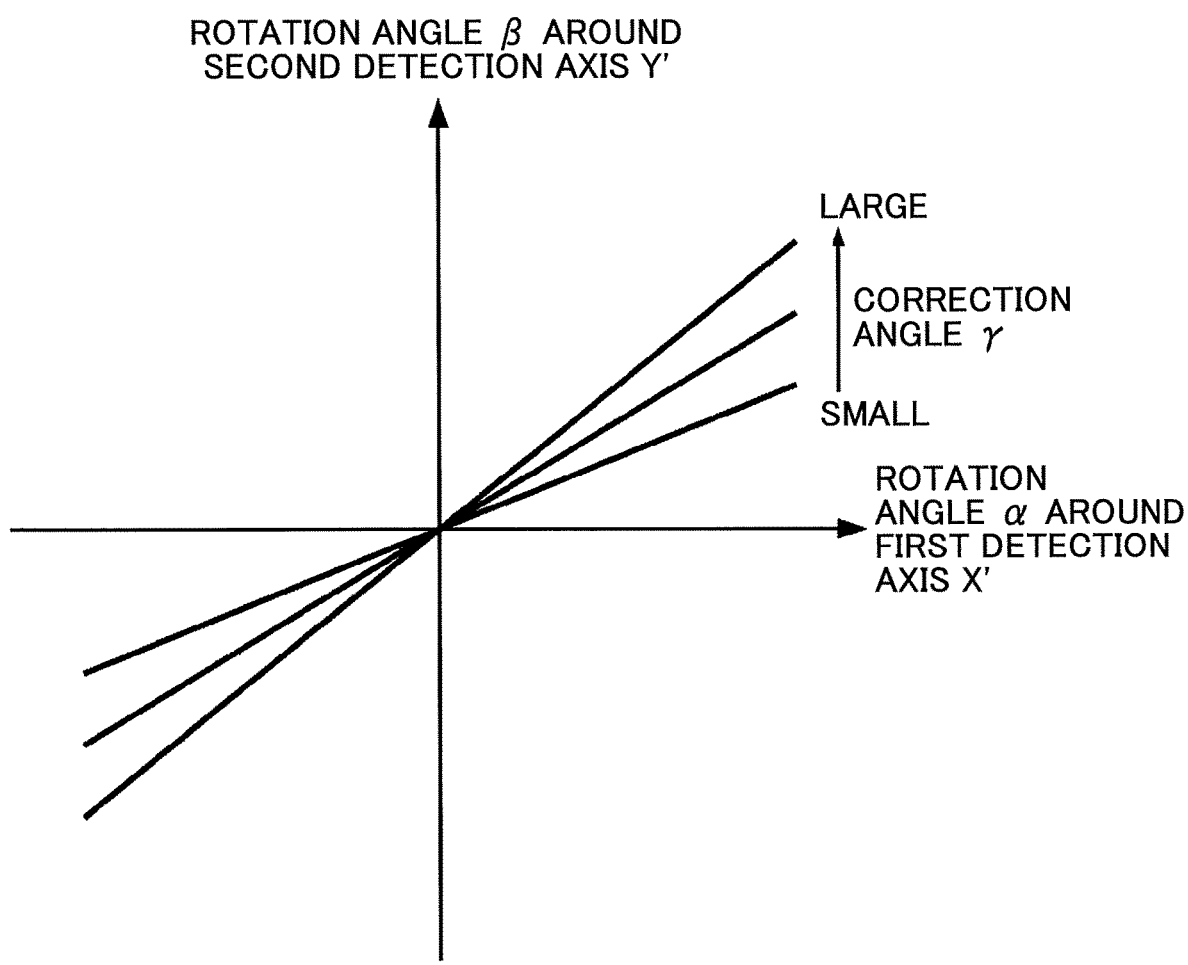
FIG. 7 is a diagram illustrating that a ratio between a rotation angle around a first detection axis and a rotation angle around a second detection axis changes in accordance with a correction angle.

FIG. 7 is a diagram illustrating that the ratio K between the rotation angle around the first detection axis X' and the rotation angle around the second detection axis Y' changes in accordance with the correction angle $\gamma$. When a predetermined motion is performed, that is, when a motion of changing the pitch angle around the first posture axis X while maintaining the roll angle around the second posture axis Y and the yaw angle around the third posture axis Z (a motion of raising and lowering one's head) is performed, as illustrated in FIG. 7, the rotation angle around the first detection axis X' and the rotation angle around the second detection axis Y' show a proportional relationship in which the slope is substantially constant. When the rotation angle around the first detection axis X' is the horizontal axis and the rotation angle around the second detection axis Y' is the vertical axis, the inclination of the straight line becomes steeper as the correction angle $\gamma$ increases. When the correction angle $\gamma$ is zero (when the first detection axis X' and the first posture axis X are parallel and the second detection axis Y' and the second posture axis Y are parallel), the rotation angle around the second detection axis Y' is substantially constant, even if the rotation angle around the first detection axis X' changes.

As described above, the ratio K between the rotation angle around the first detection axis X' and the rotation angle around the second detection axis Y' in the case of performing a predetermined motion (a motion of raising and lowering one's heady) depends on the correction angle $\gamma$. Hence, the correction angle calculation unit 22 calculates, from accelerations (Ax, Ay, Az) obtained by the acceleration sensor 10, the ratio K between the rotation angle around the first detection axis X' and the rotation angle around the second detection axis Y', and obtains the correction angle γ corresponding to the calculated ratio K.

The correction angle calculation unit 22 calculates, based on the accelerations (Ax, Ay, Az) obtained by the acceleration obtaining unit 21 when a predetermined motion (a motion of raising and lowering one's head) is being performed, the rotation angle around the first detection axis X' and the rotation angle around the second detection axis Y'. In the following, the rotation angle around the first detection axis X' may be referred to as the "first rotation angle α'" and a rotation angle around the second detection axis Y' may be referred to as the "second rotation angle β'". The first rotation angle α' and the second rotation angle β' are respectively expressed by the following formulas.

$$\alpha' = a\tan\{Ay/\sqrt{(Ax^2+Az^2)}\} \quad (5)$$

$$\beta' = a\tan(Ax/Az) \quad (6)$$

The correction angle calculation unit 22 calculates the ratio K (=β'/α') from the first rotation angle α' and the second rotation angle β', and obtains the correction angle γ based on the ratio K. As a method of obtaining the correction angle γ from the ratio K, the correction angle calculation unit 22 uses a method of referring to a data table prepared in advance in the storage unit 30, a method of directly calculating the correction angle γ from the ratio K by a predetermined approximate formula, or the like, for example.

Note that because there is a possibility that the predetermined motion (the motion of raising and lowering one's head) is not very accurate, it is preferable to use a plurality of accelerations (Ax, Ay, Az) detected at a plurality of different timings for calculating the correction angle γ. In this case, for example, the correction angle calculation unit 22 calculates, based on the accelerations (Ax, Ay, Az) obtained at the plurality of timings in the acceleration obtaining unit 21 when a predetermined motion (a motion of raising and lowering one's head) is being performed, first rotation angles α' and second rotation angles β' at the respective timings. Next, the correction angle calculation unit 22 calculates respective ratios K between the first rotation angles α' and the second rotation angles β', at the plurality of timings, and calculates an average value and a variance of the plurality of ratios K calculated for the plurality of timings. The correction angle calculation unit 22 sets, based on the calculated average value and the calculated variance value, an average value range of the ratios K. For example, the correction angle calculation unit 22 sets, as the "average value range", a range with the average value as the center and having an extent in accordance with the variance value. The correction angle calculation unit 22 specifies ratios K included in the "average value range" from the plurality of ratios K calculated for the plurality of timings, and calculates an adjusted average value that is the average value of the specified ratios K. The correction angle calculation unit 22 obtains the correction angle γ based on the adjusted average value of the ratios K. As a method of obtaining the correction angle γ from the adjusted average value of the ratios K, the correction angle calculation unit 22 uses a method of referring to a data table, a method of directly calculating by an approximate formula, or the like, for example.

Figure 8:
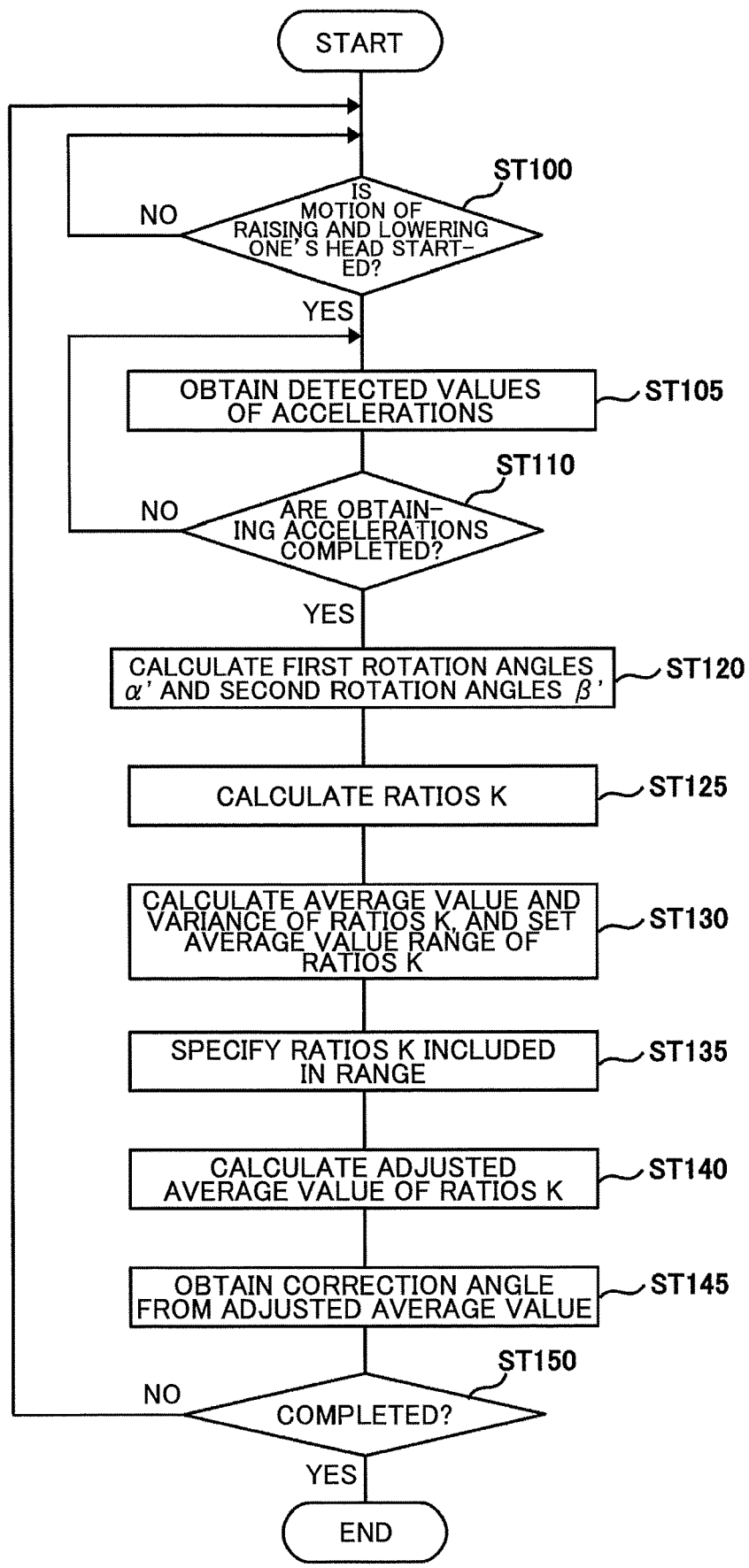
FIG. 8 is a flowchart that describes a calculation process of a correction angle in the wearable device according to a second embodiment.

FIG. 8 is a flowchart that describes a calculation process of a correction angle γ in the wearable device 1 according to the second embodiment. In the flowchart that is illustrated in FIG. 8, step ST115 in the flowchart illustrated in FIG. 5 is replaced with steps ST120 to ST145, and other steps are the same as those in the flowchart illustrated in FIG. 5. In the following, steps ST120 to ST145, which are the differences, will be described.

ST120: Upon the acceleration obtaining unit 21 completing obtaining the accelerations (Ax, Ay, Az), the correction angle calculation unit 22 calculates, based on the accelerations (Ax, Ay, Az) obtained at the plurality of timings, first rotation angles α' and second rotation angles β' at the plurality of respective timings.

ST125: The correction angle calculation unit 22 calculates, based on the first rotation angles α' and the second rotation angles β' calculated in step ST120, ratios K at the plurality of respective timings.

ST130: The correction angle calculation unit 22 calculates an average value and a variance of the plurality of ratios K calculated for the plurality of timings. The acceleration obtaining unit 21 sets, based on the calculated average value and the calculated variance value, an "average value range" of the ratios K. For example, the correction angle calculation unit 22 sets, as the "average value range", a range centered on the average value and having an extent in accordance with the variance value.

ST135: The correction angle calculation unit 22 specifies, among the plurality of ratios K calculated for the plurality of timings, ratios K included in the "average value range" set in step ST130.

ST140: The correction angle calculation unit 22 calculates, as an "adjusted average value", an average value of the ratios K specified in step ST135.

ST145: The correction angle calculation unit 22 obtains a correction angle γ based on the adjusted average value of the ratios K calculated in step ST140. For example, the correction angle calculation unit 22 obtains the correction angle γ by a method of referring to a data table prepared in advance in the storage unit 30, a method of directly calculating the correction angle γ from the ratios K by a predetermined approximate formula, or the like.

As described above, effects similar to those of the wearable device 1 according to the first embodiment can be also obtained by the wearable device 1 according to the present embodiment.

The present invention is not limited to the embodiments described above, but includes various variations.

For example, although it is determined, based on an input operation of the input unit 50, that a predetermined motion is being performed in the embodiment described above, but the present invention is not limited to this. In another embodiment of the present invention, it may be determined based on a signal input from an external device by the communication unit 40 that a predetermined motion is being performed.

Although the accelerations (Ax, Ay, Az) of the detection coordinate system 7 are converted into the accelerations (Bx, By, Bz) of the posture coordinate system 6 by rotational transformation based on a matrix as indicated by the formula (2) in the embodiments described above, the present invention is not limited to this. In another embodiment of the present invention, by rotational transformation with the third detection axis Z' as the center by quaternions, the accelerations (Ax, Ay, Az) of the detection coordinate system 7 may be converted into the accelerations (Bx, By, Bz) of the posture coordinate system 6.

Quaternion P of the accelerations (Ax, Ay, Az) detected by the acceleration sensor 10 are expressed by the following formula using unit imaginary numbers i, j, and k of the quaternion.

$$P = Ax \cdot i + Ay \cdot j + Az \cdot k \quad (7)$$

Note that the unit imaginary numbers i, j, and k satisfy the following relationships.

$$i^2 = j^2 = k^2 = -1 \quad (8)$$

$$i \cdot j = k \quad (9)$$

$$j \cdot k = i \quad (10)$$

$$k \cdot i = j \quad (11)$$

$$i \cdot j \cdot k = -1 \quad (12)$$

Quaternion Q representing the rotation of the rotation angle γ around a unit vector (Ux, Uy, Uz) is expressed by the following formula.

$$Q = \cos(\gamma/2) + i \cdot Ux \cdot \sin(\gamma/2) + j \cdot Uy \cdot \sin(\gamma/2) + k \cdot Uz \cdot \sin(\gamma/2) \quad (13)$$

Quaternion R, which is a complex conjugate number of quaternion Q, is expressed by the following formula.

$$R = \cos(\gamma/2) - i \cdot Ux \cdot \sin(\gamma/2) - j \cdot Uy \cdot \sin(\gamma/2) - k \cdot Uz \cdot \sin(\gamma/2) \quad (14)$$

Assuming that the unit vector (Ux, Uy, Uz) is a vector (0, 0, 1) parallel to the third detection axis Z', quaternion Q of the formula (13) and quaternion R of the formula (14) are expressed by the respective following formulas.

$$Q = \cos(\gamma/2) + k \cdot Uz \cdot \sin(\gamma/2) \quad (15)$$

$$R = \cos(\gamma/2) - k \cdot Uz \cdot \sin(\gamma/2) \quad (16)$$

Quaternion Pt obtained by rotating, by the rotation angle γ, quaternion P of the accelerations (Ax, Ay, Az) around the vector (0, 0, 1) that is parallel to the third detection axis Z' is expressed by the following formula.

$$Pt = Q \cdot P \cdot R \quad (17)$$

The accelerations (Bx, By, Bz) of the posture coordinate system 6 are obtained as the coefficients of the unit imaginary numbers i, j, and k in quaternion Pt obtained by the formula (17).

$$Pt = w + i \cdot Bx + j \cdot By + k \cdot Bz \quad (18)$$

In the formula, "w" is a real part of quaternion Pt. In this way, even with the method using quaternions, the accelerations (Ax, Ay, Az) of the detection coordinate system 7 can be converted into the accelerations (Bx, By, Bz) of the posture coordinate system 6.

In the embodiments described above, the correction angle γ is calculated by the correction angle calculation unit 22. However, in another embodiment of the present invention, information for the correction angle γ stored in advance in the storage unit 30 may be used, or information for the correction angle γ obtained by the communication unit 40 from the outside may be used.

Although the orientation of a human is measured in the embodiments described above, the present invention is not limited to these examples. In another embodiment of the present invention, the orientation of an animal, a machine, or the like other than a human may be measured.

DESCRIPTION OF REFERENCE SYMBOLS

1: wearable device
2: user
5: cap
10: acceleration sensor
20: processing unit
21: acceleration obtaining unit
22: correction angle calculation unit
23: posture calculation unit
30: storage unit
40: communication unit
50: input unit
X: first posture axis,
Y: second posture axis
Z: third posture axis
X': first detection axis
Y': second detection axis
Z': third detection axis
Ax: first acceleration
Ay: second acceleration
Az: third acceleration
γ: correction angle

The invention claimed is:

1. A wearable device capable of measuring a posture of a portion of a body to which the wearable device is attached, the wearable device comprising:

an acceleration sensor configured to detect respective accelerations in directions along three detection axes that are orthogonal to each other; and a posture angle calculation unit configured to calculate, based on the accelerations detected by the acceleration sensor, a posture angle around at least one posture axis of three posture axes that define a reference of the posture of the portion, to which the wearable device is attached, with respect to a direction of gravity, the three posture axes being orthogonal to each other, wherein a coordinate system obtained by rotating a detection coordinate system, defined by the three detection axes, around one of the detection axes by a correction angle and by moving the detection coordinate system in parallel matches a posture coordinate system defined by the three posture axes, the correction angle being formed between the detection axis and the posture axis, wherein the posture calculation unit converts, based on the correction angle, the accelerations in the directions along the three detection axes detected by the acceleration sensor into accelerations in directions along the three posture axes, wherein the posture calculation unit calculates, based on the accelerations at the three posture axes obtained by the conversion, the posture angle around the at least one posture axis, wherein the wearable device includes an acceleration obtaining unit configured to obtain, upon a signal being input, the accelerations detected by the acceleration sensor, the signal indicating that a predetermined motion of, while maintaining the posture angle at two of the posture axes, changing the posture angle at one of the posture axes that forms the correction angle with one of the detection axes is being performed, wherein the wearable device includes a correction angle calculation unit configured to calculate, based on the accelerations obtained by the acceleration obtaining unit when the predetermined motion is being performed, the correction angle, wherein the three posture axes are composed of a first posture axis, a second posture axis, and a third posture axis, wherein the three detection axes are composed of a first detection axis that forms the correction angle with the first posture axis, a second detection axis that forms the correction angle with the second posture axis, and a third detection axis that forms the correction angle with the third posture axis, wherein the acceleration sensor detects a first acceleration in a direction along the first detection axis, a second acceleration in a direction along the second detection axis, and a third acceleration in a direction along the third detection axis, respectively, wherein the correction angle calculation unit calculates, based on first accelerations, second accelerations, and third accelerations obtained at a plurality of timings when the predetermined motion is being performed, first rotation angles around the first detection axis and second rotation angles around the second detection axis at the respective timings, wherein the correction angle calculation unit calculates respective ratios between the first rotation angles and the second rotation angles at the plurality of timings, wherein the correction angle calculation unit calculates an average value and a variance of the ratios calculated for the plurality of timings, wherein the correction angle calculation unit sets, based on the average value and the variance, an average value range of the ratios, wherein the correction angle calculation unit specifies ratios included in the average value range, wherein the correction angle calculation unit calculates an adjusted average value that is an average value of the specified ratios, and the correction angle calculation unit obtains the correction angle based on the adjusted average value.

2. The wearable device according to claim 1,
wherein the predetermined motion is a motion of changing the posture angle at the first posture axis while maintaining the posture angle at the second posture axis and the third posture axis.

3. The wearable device according to claim 1, comprising:
a storage unit configured to store information for the correction angle used to convert the accelerations in the posture angle calculation unit or
a communication unit configured to process a communication signal including information for the correction angle used to convert the accelerations in the posture angle calculation unit.

4. A posture measurement method, by a computer of an attached wearable device, for calculating a posture angle around at least one posture axis of three posture axes that define a reference of a posture of a portion of a body, to which the wearable device is attached, with respect to a direction of gravity, the three posture axes being orthogonal to each other,
wherein the wearable device includes an acceleration sensor configured to detect respective accelerations in directions along three detection axes that are orthogonal to each other,
wherein a coordinate system obtained by rotating a detection coordinate system, defined by the three detection axes, around one of the detection axes by a correction angle and by moving the detection coordinate system in parallel matches a posture coordinate system defined by the three posture axes, the correction angle being formed between the detection axis and the posture axis,
the posture measurement method comprising:
a step of converting, based on the correction angle, the accelerations in the directions along the three detection axes detected by the acceleration sensor into accelerations in directions along the three posture axes;
a step of calculating, based on the accelerations at the three posture axes obtained by the conversion, the posture angle around the at least one posture axis;
a step of obtaining, upon a signal being input, the accelerations detected by the acceleration sensor, the signal indicating that a predetermined motion of, while maintaining the posture angle at two of the posture axes, changing the posture angle at one of the posture axes that forms the correction angle with one of the detection axes is being performed; and
a step of calculating the correction angle based on the accelerations obtained in the step of obtaining the accelerations when the predetermined motion is being performed
wherein the three posture axes are composed of a first posture axis, a second posture axis, and a third posture axis,
wherein the three detection axes are composed of a first detection axis that forms the correction angle with the first posture axis, a second detection axis that forms the correction angle with the second posture axis, and a third detection axis that forms the correction angle with the third posture axis,
wherein the acceleration sensor detects a first acceleration in a direction along the first detection axis, a second acceleration in a direction along the second detection axis, and a third acceleration in a direction along the third detection axis, respectively, and
wherein in the step of calculating the correction angle,
a first rotation angle around the first detection axis and a second rotation angle around the second detection axis are calculated based on the first acceleration, the second acceleration, and the third acceleration obtained in the step of obtaining the accelerations when the predetermined motion is being performed;
a ratio between the first rotation angle and the second rotation angle is calculated; and
the correction angle is obtained based on the ratio.

5. The posture measurement method according to claim 4,
wherein the predetermined motion is a motion of changing the posture angle at the first posture axis while maintaining the posture angle at the second posture axis and the third posture axis.

6. The posture measurement method according to claim 4,
wherein in the step of calculating the correction angle,
based on first accelerations, second accelerations, and third accelerations obtained at a plurality of timings in the step of obtaining the accelerations when the predetermined motion is being performed, first rotation angles and second rotation angles at the respective timings are calculated;
respective ratios between the first rotation angles and the second rotation angles at the plurality of timings are calculated;
an average value and a variance of the ratios calculated for the plurality of timings are calculated;
an average value range of the ratios is set based on the average value and the variance;
ratios included in the average value range are specified;
an adjusted average value that is an average value of the specified ratios is calculated; and
the correction angle is calculated based on the adjusted average value.

7. A non-transitory recording storing a program for causing a computer of an attached wearable device to execute a posture measurement method for calculating a posture angle around at least one posture axis of three posture axes that define a reference of a posture of a portion of a body, to which the wearable device is attached, with respect to a direction of gravity, the three posture axes being orthogonal to each other,
- wherein the wearable device includes an acceleration sensor configured to detect respective accelerations in directions along three detection axes that are orthogonal to each other,
- wherein a coordinate system obtained by rotating a detection coordinate system, defined by the three detection axes, around one of the detection axes by a correction angle and by moving the detection coordinate system in parallel matches a posture coordinate system defined by the three posture axes, the correction angle being formed between the detection axis and the posture axis, the posture measurement method comprising:
- a step of converting, based on the correction angle, the accelerations in the directions along the three detection axes detected by the acceleration sensor into accelerations in directions along the three posture axes;
- a step of calculating, based on the accelerations at the three posture axes obtained by the conversion, the posture angle around the at least one posture axis;
- a step of obtaining, upon a signal being input, the accelerations detected by the acceleration sensor, the signal indicating that a predetermined motion of, while maintaining the posture angle at two of the posture axes, changing the posture angle at one of the posture axes that forms the correction angle with one of the detection axes is being performed; and
- a step of calculating the correction angle based on the accelerations obtained in the step of obtaining the accelerations when the predetermined motion is being performed wherein the three posture axes are composed of a first posture axis, a second posture axis, and a third posture axis, wherein the three detection axes are composed of a first detection axis that forms the correction angle with the first posture axis, a second detection axis that forms the correction angle with the second posture axis, and a third detection axis that forms the correction angle with the third posture axis, wherein the acceleration sensor detects a first acceleration in a direction along the first detection axis, a second acceleration in a direction along the second detection axis, and a third acceleration in a direction along the third detection axis, respectively, and wherein in the step of calculating the correction angle,
- a first rotation angle around the first detection axis and a second rotation angle around the second detection axis are calculated based on the first acceleration, the second acceleration, and the third acceleration obtained in the step of obtaining the accelerations when the predetermined motion is being performed;
- a ratio between the first rotation angle and the second rotation angle is calculated; and
- the correction angle is obtained based on the ratio.

* * * * *